United States Patent [19]

Tsuda et al.

[11] 4,083,786

[45] Apr. 11, 1978

[54] APPARATUS FOR TREATING ASCITES

[75] Inventors: Nobuaki Tsuda; Naoya Kominami; Kenji Inagaki; Tamotsu Imamiya, all of Fujishi, Japan

[73] Assignee: Asahi Kasei Kogyo Kabushiki Kaisha, Osaka, Japan

[21] Appl. No.: 665,700

[22] Filed: Mar. 10, 1976

[30] Foreign Application Priority Data

| Mar. 20, 1975 | Japan | 50-32931 |
| May 29, 1975 | Japan | 50-63439 |
| Sep. 19, 1975 | Japan | 50-112589 |

[51] Int. Cl.² ............... B10D 13/00; B01D 19/00
[52] U.S. Cl. ............... 210/321 B; 210/433 M
[58] Field of Search ............ 3/1.7; 128/1 D, 214 R, 128/214 F, DIG. 3; 210/22, 23 F, 257 M, 258, 321 B, 433 M; 417/395, 416, 326, 390

[56] References Cited

U.S. PATENT DOCUMENTS

| 3,204,631 | 9/1965 | Fields | 128/DIG. 3 |
| 3,208,448 | 9/1965 | Woodward | 128/DIG. 3 |
| 3,228,877 | 1/1966 | Mahon | 210/22 |
| 3,299,826 | 1/1967 | Williams | 417/395 |
| 3,483,867 | 12/1969 | Markovitz | 128/214 R |
| 3,568,214 | 3/1971 | Goldschmied | 3/1.7 |
| 3,579,441 | 5/1971 | Brown | 210/258 X |
| 3,619,423 | 11/1971 | Galletti et al. | 210/23 F X |
| 3,791,767 | 2/1974 | Shill | 128/DIG. 3 |
| 3,865,726 | 2/1975 | Chibata et al. | 210/258 X |
| 3,908,653 | 9/1975 | Kettering | 128/214 R |

FOREIGN PATENT DOCUMENTS

2,150,838  4/1972  Germany ............... 210/23

*Primary Examiner*—Charles N. Hart
*Assistant Examiner*—Robert H. Spitz
*Attorney, Agent, or Firm*—Armstrong, Nikaido, Marmelstein & Kubovcik

[57] ABSTRACT

An apparatus for treating ascites which is safe and superior in performance and does not cause hemolysis, by removing harmful bacteria or cancer cells contained in ascites, by filtration, concentrating useful proteins, etc. contained therein and returning the resulting concentrate to living body is provided.

Said apparatus comprises an ascites-transporting means, a hemolysis-preventive means connected to said ascites-transporting means, a filter for removing bacteria and cancer cells, containing at least one membrane for filtering the ascites which has passed said hemolysis-preventive means, and a concentrating vessel containing at least one membrane for concentrating the ascites thus filtered.

14 Claims, 12 Drawing Figures

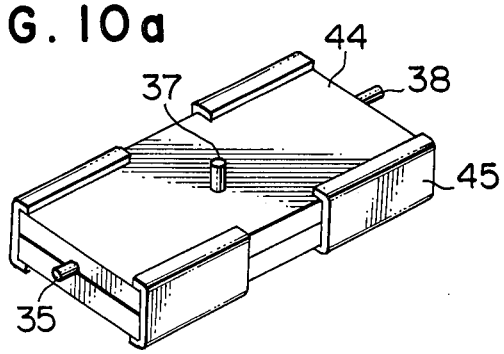
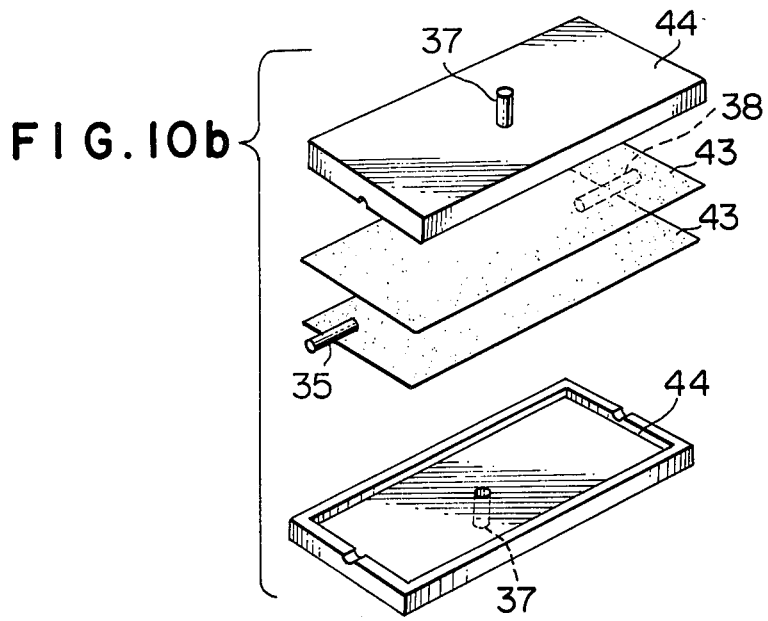

APPARATUS FOR TREATING ASCITES

DESCRIPTION OF THE INVENTION

The present invention relates to an apparatus for concentrating the useful components included in ascites of patients suffering from disease of ascites and returning the resulting concentrate to their living body.

There are many patients of cirrhosis, internal cancers, etc. who are suffering from ascites. For the patients suffering from the pressure of ascites contained in their abdomen, removal of the ascites gives them a temporary comfortable state, but a problem remains because a large amount of nutrients (particularly proteins) contained in the ascites is removed at the same time, causing heavy weakening to the patients.

In order to solve this problem, attempts to return the useful proteins contained in the ascites to a living body have recently been made, and the following two methods have been proposed now: a method of filtration and concentration carried out by means of a commercially available artificial kidney dialyser, etc. and another method of bacteria-removal or cancer cells-removal carried out by filtration by means of a commercially available membrane filter, followed by concentration. Since harmful cancer cells or bacteria contained in the ascites are concentrated and returned to a living body, the first method involves many problems for the patients. Thus this method has now been scarcely employed. The second method is very excellent in principle and safe and also considerably good in performance. According to this method, however, blood mixed into the ascites causes hemolysis at the part of this filter, and the resulting blood of hemolysis is returned to a living body. Thus this method also has not been practically employed. Since mixing of blood into the ascites often occurs, it has been the largest drawback of this method to cause hemolysis.

The object of the present invention is to provide an apparatus for treating ascites by which the above-mentioned drawbacks are overcome and which is quite safe and excellent in performance. In other words, the object is to provide an apparatus for treating ascites which enables to remove bacteria or cancer cells from the ascites, concentrate useful proteins contained in the ascites without causing hemolysis and return to a living body.

The apparatus of the present invention will hereinafter be illustrated referring to the accompanying drawings.

Figure 3:
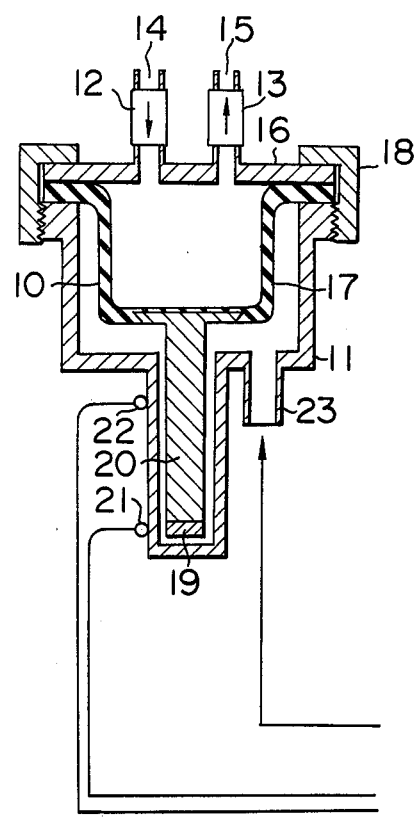
Figure 4:
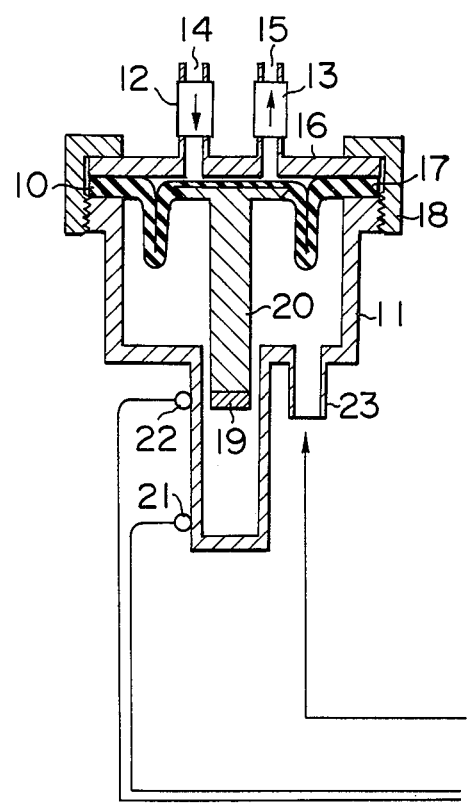

FIGS. 3 and 4 both show a longitudinal cross-sectional view illustrating the operating state of the pump.

Figure 5:
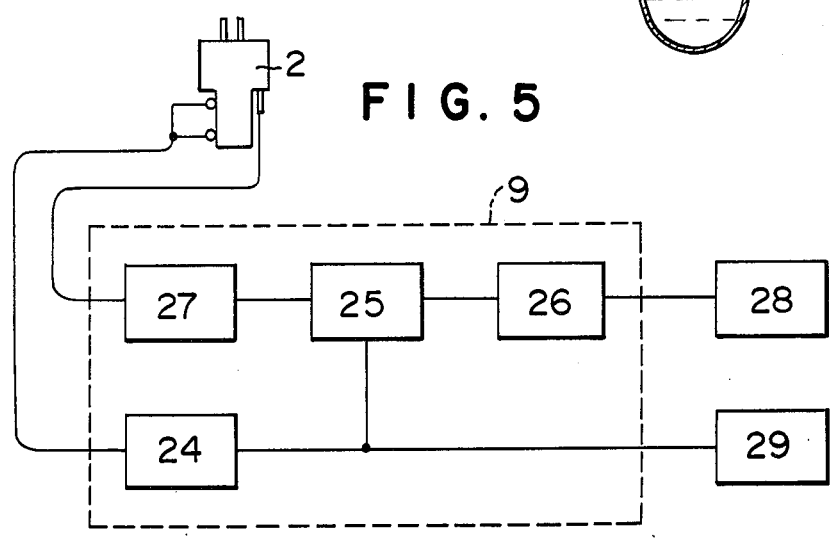

FIG. 5 shows a schematic view illustrating the ascites-transporting means (pumping means) of the present invention.

Figure 6:
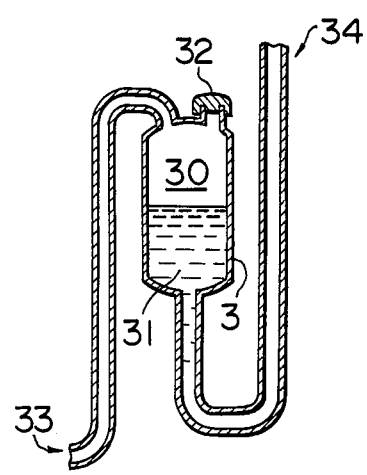
Figure 7:
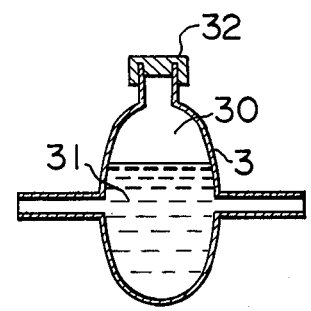

FIGS. 6 and 7 show a cross-sectional view of an embodiment of the means for preventing hemolysis, respectively.

Figure 8:
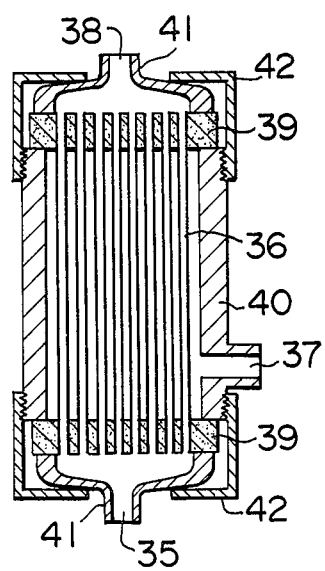

FIG. 8 shows an embodiment wherein hollow fibers consisting of an ultra-filter membrane are employed as the membrane contained in the filter in the apparatus of the present invention.

Figure 9:
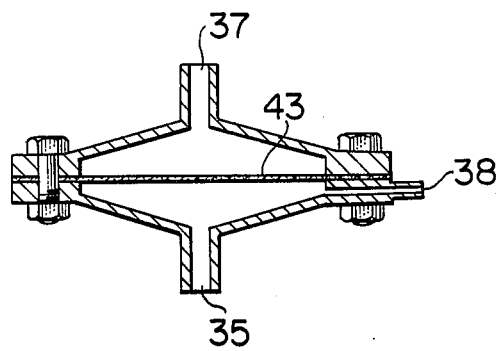

FIGS. 9, 10a and 10b show another embodiment wherein a flat membrane is employed as the membrane contained in the filter in the apparatus of the present invention.

Figure 11:
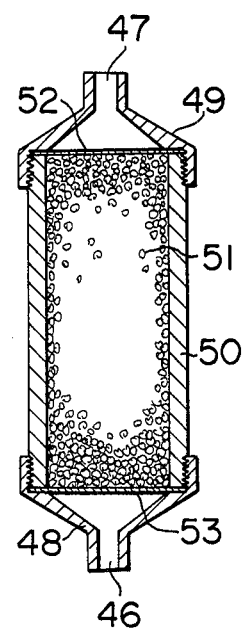

FIG. 11 shows an adsorber containing a substance capable of adhering pyrogenic substance employed in the apparatus of the present invention.

Figure 1:
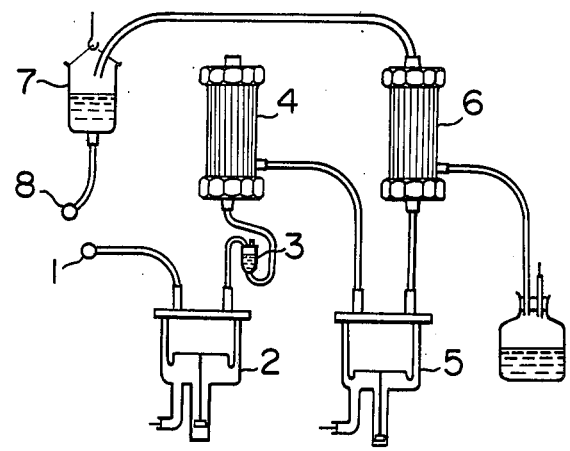
FIG. 1 shows a schematic view of one embodiment of the apparatus of the present invention.
Figure 2:
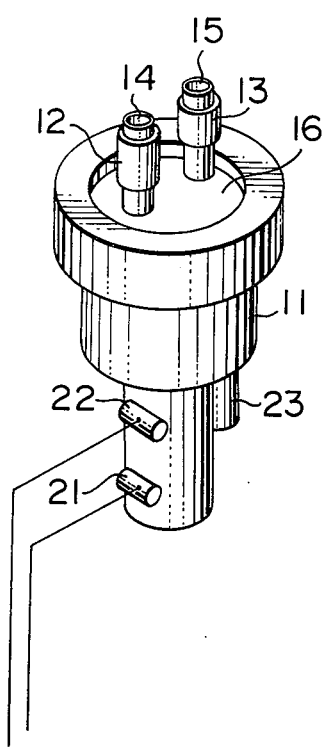
FIG. 2 shows a perspective view of one embodiment of the ascites-transporting means (pump) employed in the apparatus of the present invention.

In FIG. 1, ascites discharged from a living body is introduced into ascites inlet 1; sent by means of pump 2; passed through hemolysis-preventive means 3; filtered by means of filter 4 for removing bacteria and cancer cells; and concentrated by means of concentrator 6. The resulting concentrate of ascites is collected in storing bottle 7 and thereafter taken out of ascites-taking out exit 8 and intravenously infused into the living body.

In this process, harmful bacteria or cancer cells contained in the ascites are removed and useful proteins (albumin, globulin, etc.) are concentrated to 2 - 10 times the original concentration and intravenously infused to patients.

The pumps used as ascites-transporting means in the apparatus of the present invention, performs a function of taking out ascites from the abdomen of a living body and transporting it to various parts of the apparatus. It is not desirable to take out the ascites forcibly from a living body because this is a great burden to the patients. Thus it is necessary to take out the ascites in accordance with the discharging capacity of the patients themselves. As for such pumps, the following pumps designed for a living body are most desirable:

(1) a pumping apparatus for a living body which has (i) a pump constructed with (a) a variable vessel whose inner volume is variable and provided with an inlet and an outlet for a body fluid, each having a check valve, and (b) a gas pressure vessel having an opening for introducing and discharging a gas, said variable vessel and said gas pressure vessel each forming an independent chamber separated from each other by the variable part of said variable vessel as a partition, and (ii) a controller which repeats automatically the operations of sending a gas into said gas pressure vessel when a given amount of the body fluid is fed into said variable vessel of said pump, and discharging the gas from said pressure vessel when the amount of the body fluid is reduced down to a certain definite amount; and (2) a pumping apparatus for a living body which has (i) a pump constructed with (a) a variable vessel whose inner volume is variable and provided with an inlet and an outlet for a body fluid, each having a check valve, and (b) a gas pressure vessel having an opening for introducing and discharging a gas, said variable vessel and said gas pressure vessel each forming an independent chamber separated from each other by the variable part of said variable vessel as a partition and (ii) a controller which repeats automatically the operations of sending a gas into said gas pressure vessel when a given amount of the body fluid is fed into said variable vessel of said pump, and discharging the gas from said pressure vessel when the amount of the body fluid is reduced down to a certain definite amount, and (iii) a timer which regulates the interval of time from the completion of the feed of a definite amount of body fluid into the variable vessel to the starting of the next feeding of said body fluid into said variable vessel.

Such a pumping apparatus will be hereinafter illustrated referring to FIGS. 2, 3, 4 and 5.

In the first place, the pumping apparatus of the present invention consists of pump 2 and controller 9 (see FIG. 5).

Pump 2 is constructed with variable vessel 10 into which body fluid is introduced and gas pressure vessel 11 (see FIG. 3). Variable vessel 10 provided with an inlet for introducing body fluid 14 and an exit for discharging it 15, each having check valve 12, 13, an upper plate 16 and a variable (deformable) part 17 constituting a deformable vessel, and is clamped onto gas pressure vessel 11 by means of cap 18 to form an independent space. Gas pressure vessel 11 has connecting rod 20 connected with variable vessel 10 and provided with magnet 19, lead switches 21 and 22 actuated by means of magnet 19 and further port 23 through which a gas sent from controller 9 is introduced and discharged. Thus, the pump of the present invention includes two chambers which are independent from each other and separated by variable part 17 as a partition.

Since body fluid contacts with upper plate 16, the plate must be of a safe and non-poisonous material of usual plastics or others although it is not necessary to be a particular definite material. Check valves 12, 13 are those through which body fluid is caused to flow unidirectionally. Usual check valves such as those having therein a ball of nylon, polyester or the like, an electromagnetic valve capable of performing the function of check valve as a substitute, etc. may be useful, but it is necessary that they are non-poisonous and superior in safety since body fluid passes therethrough. As for the material of variable part 17, although it varies depending upon the shape or design of the part, if a cup form one as shown in FIG. 3 is employed, rubbery materials such as silicone rubber, natural rubber, or the like, which is superior in safety from both hygienic and poisonous viewpoints may be conveniently used. If a bellows form one is employed, any materials may be useful so long as they are deformable in accordance with gas pressure and can constitute the variable part, such as polyethylene. However, it is necessary that the materials are safe from medical viewpoint. As for variable part 17 and upper plate 16, besides the above-mentioned structure clamped by means of cap 18, those which are bonded into one block by adhesion or other means may be employed, and their materials may be the same or different so long as they satisfy the above-mentioned requirements. The parts which contact with body fluid are preferably those which are disposable and simple and also of a cheap material. Lead switches 21 and 22 actuated by means of magnet 19 of the gas pressure vessel controls the introduction into and discharge from the gas pressure vessel, of gas. In place of this mechanism, a photo-electric tube or other detecting mechanisms may be employed. In short, those which actuate the switches at the upper limit point and the lower limit point responsive to the upper and lower limits of a definite amount of gas, by the interlocking with the inner volume of variable vessel 10, may be employed.

Controller 9 controls the flow amounts of gas introduced into and discharged from gas pressure vessel 11 of the pump, whereby the discharging speed and the pressure of body fluid are controlled. As one embodiment there is illustrated an apparatus consisting of relay 24, electromagnetic valve 25, pressure-controlling means 26 and flow amount-controlling means 27 (see FIG. 5). In this Figure, numerals 28 and 29 show a gas source and an electric source, respectively.

The actuation of the pumping apparatus shown in the drawings will be illustrated.

When the pumping apparatus is energized by turning on a switch, lead switch 21 is actuated by the function of magnet 19 adjacent thereto, as shown in FIG. 3, to actuate electromagnetic valve 25 through relay 24 of controller 9, whereby gas is introduced into gas pressure vessel 11 through port 23 for introducing and discharging gas to exert pressure to variable part 17. Thus, the inner volume of variable vessel 10 is reduced and connecting rod 20 connected with variable vessel 10 is elevated to form a state shown in FIG. 4. At this time, the air which has been initially filled in variable vessel 10 is discharged to the outside through check valve 12 and exit for discharging body fluid 14. At this time, lead switch 22 is actuated by means of magnet 19 which has now occupied closer position by elevation of connecting rod 20, to actuate electromagnetic valve 25 through relay 24, whereby the introduction of gas under pressure is stopped, the inner pressure is released and gas is discharged. At this point, body fluid discharged from a living body is introduced into variable vessel 10 via inlet for introducing body fluid 15 and check valve 13. Body fluid is introduced into variable vessel 10 in proportion to the pressure and discharging force of body fluid from the inside of living body and also by means of the restoring force to the original state, of variable vessel 10, the weight of connecting rod 20 connected with variable vessel 10, and other forces. As body fluid is introduced into variable vessel 10, connecting rod 20 is lowered to recover the state shown in FIG. 3. Thus, FIG. 3 shows the initial state of variable vessel 10 the inside of which is empty and the state thereof where body fluid is filled up to a definite amount.

When body fluid is introduced into variable vessel 10 to lower connecting rod 20, magnet 19 provided in the connecting rod again actuates lead switch 21. Accordingly, body fluid inside variable vessel 10 is discharged to the outside via check valve 12 and exit for discharging body fluid 14. When a definite amount of body fluid is discharged, the inner volume of variable vessel 10 is reduced to form the state shown in FIG. 4. Such procedures are repeated and the pumping apparatus is automatically actuated.

It is advantageous to provide a means for controlling the time at which body fluid begins to be again fed into the variable vessel after a definite amount of body fluid has been fed into the variable vessel, for the following reason: As an example of the above-mentioned means, a case where a timer is provided will be illustrated. When the lower lead switch is actuated to reduce the inner volume of the variable vessel, a timer can control the time during which the connecting rod connected therewith is being elevated. Accordingly, in case where the timer is absent, only the upper and lower limits of the inner volume of the variable vessel can be controlled. Whereas, in case where the timer is provided, it is possible to set the timer to a time corresponding to any intermediate point between the upper and lower limits of the inner volume and also to a time corresponding to a volume exceeding the lower limit, whereby body fluid can be taken out in accordance with the discharge speed of body fluid from a living body.

Since the pumping apparatus has the above-mentioned construction, the apparatus is useful particularly in the case where body fluid must not be rapidly taken out, or the case where body fluid is transported in accordance with the discharging capability of living body from the inside thereof. Further the apparatus is also useful in the case where body fluid is continuously subjected to filtration-concentration through a membrane. Furthermore, the apparatus is also useful as a pump for transporting a taken-out body fluid or as a pump for pressurizing it. Further, when body fluid is taken out of living body, the pumping apparatus enables to relieve the shock of living body and take out the fluid smoothly. Thus, failure due to forcible taking-out of body fluid by means of e.g. a conventional pump does not occur, and the taking-out can be carried out safely. In case of usual pumps, special labour and time are necessary for taking out body fluid from living body, whereas the pumping apparatus of the present invention can be easily operated in order to attain the object. Although this pumping apparatus for living body may be most suitable for the pump of the present invention, a commercially available roller pump, etc. may be also employed for the pump of the apparatus of the present invention if they are adequately controlled and carefully operated.

In the apparatus of the present invention, the means for preventing hemolysis is provided between the means for transporting ascites and the filter for bacteria-removal or cancer cells-removal. Since ascites causes hemolysis in the filter, the means for preventing hemolysis should be provided at a location nearer to the inlet for introducing ascites, of the filter. As for means for preventing hemolysis, a means for weakening the hemolysis-forming property or a means for removing bubbles, etc. contained in ascites is employed. Bubbles contained in ascites becomes a cause of hemolysis. The most desirable means for preventing hemolysis is the one having a part in which air is collected when ascites is introduced, and a part in which the amount of air thus collected is controlled. The apparatus will be illustrated below referring to FIGS. 6 and 7.

In FIG. 6, numeral 30 shows a collecting part of air formed when ascites 31 is introduced and numeral 32 shows a part for controlling the amount of air collected. Any structure of controlling part 32 will be useful so long as it enables to control the amount of air optionally. FIG. 6 illustrates a structure in which controlling part 32 consists of a rubbery part and the amount of air is controlled simply and aseptically using a syringe. Numerals 33 and 34 show the connecting parts for ascites inlet side and for the filter side, respectively. FIG. 7 also shows a means for preventing hemolysis, having collecting part of air 30 and controlling part of air 32 as in FIG. 6. In addition to these means, any of those having such a construction that the bubbles contained in ascites can be always removed aseptically may be employed.

The filter for bacteria-removal or cancer cells-removal has a membrane having a pore size which cuts the passage of bacteria or cancer cells but allows the passage of proteins (albumin, globulin, etc.) useful for living body, and a vessel containing said membrane. As for the material of the membrane, any of those having the above-mentioned pore size which is not poisonous and not harmful to living body may be employed. For example, cellulose acetate, polyacrylonitrile, etc. may be enumerated. As for the shape of the membrane, either a flat membrane such as millipore membrane or a membrane in the form of hollow fiber may be employed, but the latter membrane in the form of hollow fiber is advantageous in that it has a higher treating capacity for ascites and the blood contained in ascites is hard to cause hemolysis in contact with the membrane.

The pore size of the membrane may be 0.2 $\mu$ or less, preferably in the range of 0.2 $\mu$ - 0.01 $\mu$, because it can remove bacteria or cancer cells in case of such pore sizes.

The membrane loses its filtration efficiency during the treatment of ascites. The reason is that substances which do not pass through the membrane (such as bacteria, cancer cells, etc.) adhere onto the surface of the membrane. The extent of this phenomenon is larger in the case of a flat membrane, and if the concentration of the substances which do not permeate through the membrane is too high, the membrane is brought to a substantially unusable state. However, such a problem may be solved by providing in a vessel containing the filter, an opening for removing the substances which are impermeable through the membrane, by flushing. Further, by providing such an opening for removal by flushing in the vessel, such secondary advantages may be obtained that a concentrate of the substances which are impermeable through the membrane (e.g. cancer cells) can be obtained whereby cell test can be readily carried out, etc.

The structure of the filter provided with a flushing opening will be illustrated referring to FIGS. 8, 9, 10a and 10b.

The filter shown in FIG. 8 is such a type of filter that inlet of ascites 35 communicates with the hollow parts of a plurality of hollow fibers 36. Thus, exit for taking out ascites 37 is provided on the side partitioned from said inlet of ascites 35 by way of the membranes. On the other hand, flushing opening 38 is provided on the side of the open ends of hollow fibers 36.

In the filter of this type, ascites introduced from inlet of ascites 35 passes through the hollow parts of hollow fibers 36, and is subjected to ultra-filtration from the hollow parts of hollow fibers to the outside of the fibers, and the useful components such as proteins, etc. are taken out from exit of ascites 37. Substances which do not permeate from the hollow parts of hollow fibers to the outside (bacteria, cancer cells, etc.) are collected within the hollow fibers. Since these substances reduce the filtration efficiency of hollow fibers, they are removed from flushing opening 38 from time to time. At the same time, bubbles which are collected in the inside of the hollow fibers and become a cause of hemolysis are also removed. A plurality of inlets of ascites, exits of ascites and flushing openings may be provided in the vessel.

As shown in FIG. 8, such a filter for treating ascites may be prepared, for example, by adhering together the ends of hollow fibers 36 with adhesive 39, clamping the resulting adhered part with body of vessel 40 and nozzle of vessel 41, and further clamping body of vessel 40 with caps of vessel 42 provided with screws, to fix all together. Although both the ends of hollow fibers are together adhered with an adhesive and fixed onto the vessel containing them as shown in FIG. 8, in general, at least one end of hollow fibers may be fixed.

As for the adhesive for adhering the hollow fibers together, materials which are not poisonous and not harmful to living body may be employed. For example, silicone resin, urethane resin, epoxy resin, etc. may be employed.

As another embodiment of the filter of the present invention using hollow fibers, such a type may be mentioned that ascites is filtered from the outer side (outer wall) of hollow fibers to the hollow parts thereof. In this case, the exit for taking out filtered ascites is provided at a location communicating with the hollow parts of hollow fibers, and the inlet and the flushing opening of ascites are provided on the side partitioned from said exit for taking out filtered ascites, by way of the membranes.

Next, the case where a flat membrane is employed for the membrane will be illustrated referring to FIG. 9. Inlet of ascites 35 and exit for taking out ascites 37 are fixed onto separate chambers partitioned by way of flat membrane 43, as in the case where hollow fibers are employed. Flushing opening 38 is fixed onto the same chamber as that containing inlet of ascites 35, among the above-mentioned chambers partitioned by way of flat membrane 43. In this filter, ascites is introduced from exit of ascites 35, filtered by membrane 43, where unnecessary components are cut and useful proteins are permeated, and taken out from exit for taking out ascites 37. Since the unnecessary components cut at membrane 43 gradually reduces the above-mentioned membrane characteristics, they are flushed from time to time from flushing opening 38.

There is also an embodiment shown in FIGS. 10a and 10b in which a flat membrane is employed as in the above-mentioned case. In the case of this Figure, however, two flat membranes 43 are clamped with two plates 44 each provided with exit of ascites 37, and at the same time, inlet of ascites 35 and flushing opening 38 are fixed together between the above-mentioned two membranes 43, by way of fixing means 45.

For sending ascites freed of bacteria or cancer cells to a concentrating vessel where the ascites are concentrated to a given concentration, a pump may be employed. This pump, however, may be not always necessary. For example, when the above-mentioned pump for taking out ascites is substituted for it, it may be unnecessary. This pump for transportation may be the same as or different from the pump for taking out ascites, but should not, of course, be poisonous and harmful to the ascites flowing through the inside.

The concentrating vessel is used for concentrating proteins contained in the ascites freed of bacteria or cancer cells. It contains at least one membrane which is superior in water-drainage and does not allow proteins (albumin, globulin, etc.) useful for living body to pass. In general, membranes employed for artificial kidney, such as those of polyacrylonitrile, cellulose acetate, cuproammonium rayon, polymethyl methacrylate, etc. may be employed. From the viewpoint of treating capacity and simplicity, it is preferable to employ a hollow fiber form membrane.

The concentrated ascites is collected in a storing bottle and instilled intravenously at an almost constant rate. This storing bottle plays a role of temporarily storing the concentrated ascites to be infused. For example, commercially available polyethylene bottle for a physiological solution of sodium chloride, etc. may be employed.

When returning of ascites to living body is practiced by means of such an apparatus, a certain extent of fever occurs. Although such a fever is not so serious as to threaten human life, it is a considerable burden to patients. In such a case, if a substance capable of adsorbing pyrogenic substance is introduced into the circuit of the ascites-treating apparatus, the fever will be subdued.

An example of an adsorber containing a substance capable of adsorbing pyrogenic substance will be illustrated referring to FIG. 11.

In a vessel constructed by connecting nozzle 48 provided with inlet of ascites 46 and nozzle 49 provided with exit of ascites 47, to body 50, by means of screws, there is contained substance 51 capable of adsorbing pyrogenic substance, which is isolated by filters 52, 53 in order to prevent it from escaping.

It will serve the purpose to place the substance capable of adsorbing pyrogenic substance anywhere between inlet for introducing ascites 1 and exit for discharging ascites 8 in FIG. 1. Further, the substance capable of adsorbing pyrogenic substance should not be necessarily to be in the state placed in a vessel as shown in FIG. 11, but it may be placed in the manner distributed over the whole or at a part of the circuit. Alternatively, the substance may be introduced into the membrane (hollow fiber membrane, flat membrane, etc.) of the filter for bacteria-removal or cancer cells-removal, by means of kneading or the like into the membrane, or the like, or it may be contained in the filter or the concentrating vessel. In short, it will be sufficient if the substance capable of adsorbing pyrogenic substance is existent somewhere in the circuit.

As for the adsorbent used in the apparatus of the present invention, although any of those capable of adsorbing and removing pyrogenic substance may be employed, activated carbon is exemplified as a representative adsorbent.

Although there are various kinds of activated carbon depending on the preparation methods, any of those having adsorptivity may be employed (e.g. charcoal, activated carbon from coconut shell, etc.). Although any shape of active carbon, e.g. powder, granule, etc. may be employed, it is necessary to pay attention so as not to allow carbon powder to be freed and enter living body. Further, activated carbon coated with various high molecular weight compounds (such as cellulose, collodion, gelatine, etc.), microcapsulated activated carbon, microcapsulated active carbon which are coated with albumin or the like in double or triple layers, etc., may be employed. In short, it may be sufficient if the adsorbent is a substance capable of adsorbing and removing pyrogenic substance which is medically safe, not poisonous and not harmful. Practically, the adsorbent is used after sterilization according to various methods. Further, the adsorbent must be a substance which is unquestionable in safety tests such as acute poison test, pyrogen test, hemolysis test, etc.

In addition to the foregoing, the circuit employed in the apparatus of the present invention, particularly the parts contacting directly to ascites, must be all disposable, and the materials employed may be safe and not poisonous.

EXAMPLE 1

Ascites containing blood was treated using the ascites-treating apparatus shown in FIG. 1.

As the ascites-transporting pump, two pumping apparatuses which take out ascites in accordance with the discharging capacity of living body and transport it, were employed.

As the membrane contained in the filter for bacteria-removal or cancer cells-removal, hollow fibers of cellulose acetate (outer diameter: 500 μ, inner diameter: 300 μ, effective length: 190 mm, 2,100 filaments) were employed.

As the membrane contained in the concentrating vessel, hollow fibers of polyacrylonitrile (outer diameter: 1,400 μ, inner diameter: 800 μ, effective length: 230 mm; 650 filaments) were employed.

As the means for preventing hemolysis, the apparatus shown in FIG. 6 was employed.

As a result, about 3 l of ascites could be treated in about 2 hours. The resulting concentrated ascites was aseptic, and proteins were concentrated to 2.5 times the original concentration, and also no hemolysis component of blood was observed in the concentrated ascites. Further, when this concentrated ascites was infused intravenously to a patient, no trouble occurred, and about 60 g of proteins could be returned to the body of the patient.

COMPARATIVE EXAMPLE 1

Using the same apparatus as in the above Example 1, but removing the means for preventing hemolysis, an expriment was carried out under almost the same conditions as those of Example 1. As a result, the resulting concentrated ascites was red-colored, and hemolysis was clearly observed. Thus, intravenous infusion to patient was stopped.

EXAMPLE 2

Using a filter for bacteria-removal or cancer cells-removal, as shown in FIG. 8, containing 2,100 filaments of hollow fiber of cellulose acetate (outer diameter: 500 μ; inner diameter: 300 μ, effective length: 190 mm), ascites was treated as follows:

Filtration was carried out by introducing an ascites in which a slight amount of blood was mixed, from the exit of ascites, under a pressure of 0.3 Kg/cm$^2$, while flushing about 100 ml every about 30 minutes from the flushing opening. As a result, the initial filtration velocity 1,800 ml/hr was reduced down to 1,400 ml/hr in about 2 hours (i.e., the reduction rate was about 20%).

The resulting filtered ascites taken out from the exit of ascites was a light yellow and transparent solution of proteins and was aseptic.

COMPARATIVE EXAMPLE 2

Using the same filter for bacteria-removal or cancer cells-removal as in Example 2, except that the flushing opening was absent, ascites was treated under the same conditions as in Example 2, except that no flushing was carried out. As a result, the initial filtration velocity 1,800 ml/hr was reduced down to 900 ml/hr in about 2 hours (i.e., the reduction rate was as large as 50%). Also, the filtered ascites obtained from the exit of ascites was slightly light red. It is evident that hemolysis occurred.

EXAMPLE 3

An apparatus wherein an adsorber as shown in FIG. 11, containing 500 g of an activated carbon made of coconut shell having 25 – 40 meshes, as a substance capable of adsorbing pyrogenic substance, was provided between the concentrating vessel and the storing bottle in the circuit of the ascites-treating apparatus as shown in FIG. 1, was employed.

An ascites taken out from a living body was caused to flow into the circuit through the inlet for introducing ascites, at a velocity of 1 l/hr, to carry out filtration and concentration. The resulting ascites was intravenously infused in the living body at a velocity of about 350 ml/hr, for about 5 hours. No fever due to pyrogen was observed.

COMPARATIVE EXAMPLE 3

Ascites was treated using the same apparatus as in Example 3 except that the substance capable of adhering pyrogenic substance was not contained, and under the same conditions as in Example 3. As a result, the body temperature of a living body increased from 36.5° C prior to the use of the apparatus to about 38° C in about 1 hour after the intravenous infusion started. Thus fever due to pyrogen was evidently observed.

EXAMPLE 4

Ascites was treated using the same apparatus as in Example 3 and under the same conditions as in Example 3, except that an activated carbon made of coconut shell having 25 – 40 meshes, which have been coated with collodion film, then microcapsulated and further coated with albumin was employed as the substance capable of adhering pyrogenic substance. As a result, no fever due to pyrogen was observed.

According to the apparatus of the present invention, even in case where blood is mixed in ascites, a concentrated ascites wherein proteins have been concentrated and harmful bacteria or cancer cells have been removed, is obtained and the resulting ascites can be intravenously infused. Thus, this apparatus can afford a great advantage to patients suffering from disease of ascites.

What is claimed is:

1. An apparatus for treating ascites including protein and contaminated with at least one member of the group consisting of blood, cancer cells and bacteria, said apparatus comprising:
    (a) an ascites introducing means for carrying ascites from a body into said apparatus;
    (b) an ascites transporting means coupled to said introducing means for supplying the force to carry said ascites through said apparatus;
    (c) a first filter means for removing bacteria and cancer cells from said ascites, said first filter means including at least one first membrane means for allowing protein to pass therethrough and for blocking the passage of bacteria, cancer cells and other substances of similar size;
    (d) a hemolysis preventative means coupled between the output of said transporting means and the input of said first filter means for removing air bubbles from said ascites whereby hemolysis caused by the mixture of air bubbles with the filtered ascites is prevented;
    (e) an ascites concentrating means, coupled to the output of said first filter means, said ascites concentrating means including a second membrane means for passing substances of a size different than the size of the substances passed by said first membrane means for blocking the protein in said ascites to thereby form a protein concentrated ascites;
    (f) ascites discharging means, coupled to said ascites concentrating means, for receiving said protein concentrated ascites and returning said protein concentrated ascites to the body.

2. An apparatus for treating ascites as set forth in claim 1 wherein said transporting means comprises:
    (a) a pump having a variable vessel, the inner volume of which is variable and provided with an inlet and an outlet for a body fluid, said inlet and outlet each having a check valve, and a gas pressure vessel with an opening for introducing and discharging a gas, said variable vessel and said gas pressure vessel each forming independent chambers separated from each other by a partition formed by the variable part of said variable vessel;

(b) a controller means including first and second lead switches for automatically repeating the operations of sending a gas into said gas pressure vessel upon the actuation of said first lead switch when a given amount of the body fluid is fed into said variable vessel and discharging the gas from said pressure vessel upon the actuation of said second lead switch when the amount of the body fluid is reduced to a predetermined amount wherein said first and second lead switches are fixed to a cylinder having a movable rod therein said rod having a magnet fixed thereto, said movable rod being attached to the bottom of said variable part of said variable vessel to displace said variable part when said rod moves.

3. An apparatus according to claim 2, wherein the variable part of the variable vessel contained in said pumping apparatus consists of a silicone resin.

4. An apparatus for treating ascites as set forth in claim 1 wherein said transporting means comprises:

(a) a pump having a variable vessel, the inner volume of which is variable and provided with an inlet and an outlet for a body fluid, said inlet and outlet each having a check valve, and a gas pressure vessel with an opening for introducing and discharging a gas, said variable vessel and said gas pressure vessel each forming independent chambers separated from each other by a partition formed by the variable part of said variable vessel;

(b) a controller means including first and second lead switches for automatically repeating the operations of sending a gas into said gas pressure vessel upon the actuation of said first lead switch when a given amount of the body fluid is fed into said variable vessel and discharging the gas from said pressure vessel upon the actuation of said second lead switch when the amount of the body fluid is reduced to a predetermined amount wherein said first and second lead switches are fixed to a cylinder having a movable rod therein said rod having a magnet fixed thereto, said movable rod being attached to the bottom of said variable part of said variable vessel to displace said variable part when said rod moves; and (c) a timer means for regulating the time from the completion of the feed of a definite amount of body fluid into said variable vessel to the starting of the next feeding of said body fluid into said variable vessel.

5. An apparatus according to claim 4 wherein the variable part of the variable vessel contained in said pumping apparatus consists of a silicone resin.

6. An apparatus according to claim 1 wherein said hemolysis-preventive means comprises a part for collecting air and a part for controlling the amount of air thus collected.

7. An apparatus according to claim 1 wherein said filter comprises a vessel containing said membrane and provided with an inlet and an exit of ascites having permeated through said membrane and an opening for flushing substances which do not permeate therethrough.

8. An apparatus according to claim 1 wherein said filter comprises a vessel containing a plurality of hollow fiber type membranes and provided with an inlet and an exit of ascites having permeated through said membranes and an opening for flushing substances which do not permeate therethrough, said membranes being fixed in liquid-tight manner onto said vessel at at least one end of said membranes.

9. An apparatus according to claim 8, wherein said membranes consist of cellulose acetate or polyacrylonitrile.

10. An apparatus according to claim 8, wherein said membranes consist of cellulose acetate having a pore size of $0.2\ \mu - 0.01\ \mu$.

11. An apparatus according to claim 8, wherein said liquid-tight fixing is carried out with an adhesive selected from the group consisting of silicone resin, urethane resin and epoxy resin.

12. An apparatus according to claim 1, wherein the membrane contained in said concentrating vessel is hollow fiber consisting of an ultrafilter membrane.

13. An apparatus according to claim 12, wherein said hollow fiber is of a material selected from the group consisting of polyacrylonitrile, cellulose acetate and cuproammonium rayon.

14. An apparatus according to claim 1, wherein a substance capable of adsorbing pyrogenic substance is contained in the circuit of the apparatus.

* * * * *